United States Patent [19]

Ward

[11] 4,279,352

[45] Jul. 21, 1981

[54] MOLDED INJECTION SITE

[75] Inventor: Gary A. Ward, Round Lake, Ill.

[73] Assignee: Baxter Travenol Laboratories, Inc., Deerfield, Ill.

[21] Appl. No.: 129,857

[22] Filed: Mar. 13, 1980

Related U.S. Application Data

[63] Continuation of Ser. No. 19,399, Mar. 12, 1979, abandoned.

[51] Int. Cl.³ .............................................. B65D 41/20
[52] U.S. Cl. ......................................... 215/247; 150/8; 215/321
[58] Field of Search ............... 215/247, 248, 249, 317, 215/321, 320, DIG. 3; 150/8

[56] References Cited

U.S. PATENT DOCUMENTS

| 2,085,950 | 7/1937 | Busch | 215/317 X |
| 2,372,182 | 3/1945 | Barr | 215/247 X |
| 2,947,432 | 8/1960 | Marcel | 215/321 |
| 3,118,557 | 1/1964 | Bogikes | 215/247 |
| 4,133,441 | 1/1979 | Mittleman | 215/320 X |
| 4,153,173 | 5/1979 | Ward et al. | 215/232 |

FOREIGN PATENT DOCUMENTS

| 449030 | 6/1949 | Italy | 215/320 |
| 477152 | 1/1953 | Italy | 215/320 |
| 471834 | 9/1937 | United Kingdom | 215/320 |

Primary Examiner—Donald F. Norton
Attorney, Agent, or Firm—Paul C. Flattery; John P. Kirby, Jr.; Garrettson Ellis

[57] ABSTRACT

A unitary molded injection site comprising a central, needle-receiving portion and a skirt portion may be assembled onto a support tube by temporarily convoluting the skirt portion about the central portion to expose its inner surface; bringing the end of the support tube adjacent to the inner surface; and bringing the skirt portion back toward its original, unstressed configuration, to surround the end portion of the tube in telescoping relation. An advantage of this is that the injection site is positioned on the support tube in relatively unstressed condition. Furthermore, the skirt portion may define on its inner surface a plurality of sealing rings adapted to sealingly bear against the support tube.

5 Claims, 3 Drawing Figures

MOLDED INJECTION SITE

This application is a continuation of U.S. application Ser. No. 019,399, filed Mar. 12, 1979, now abandoned.

BACKGROUND OF THE INVENTION

In U.S. Pat. No. 4,133,441 a unitary, molded injection site is shown residing upon the end of a flared tube, which may be an access tube for a flexible parenteral solution container, a blood bag, a solution or blood administration set, a blood set for a dialyzer or blood oxygenator, or the like. The injection site of the above-cited patent is molded in unitary manner, and is formed of selfsealing, piercable resilient material, comprising a central, needle-receiving portion, and a skirt portion carried by the central portion and extending in a direction away from the central portion.

To install the injection site of the cited patent on a tubular member, the needle-receiving portion is positioned on the tubular member, and then the generally cylindrical skirt portion is convoluted out of its original, unstressed configuration into a position which surrounds the outer end of the tubular portion.

Rings, positioned circumferentially about the skirt portion, are originally molded on the inside of the skirt or tubular portion, but in the stressed, installed position, they reside on the outside of the structure to serve as compression members to assist in holding the skirt portion in squeezing relation to the tube.

In accordance with this invention, a unitary, molded injection site for carrying upon a support tube is provided in which the tendency of the injection site to "pop off" of the tube end is significantly reduced. This is so because the injection site of this invention resides on the tube end in relatively unstressed configuration, so that there are only greatly reduced forces, if any, urging the "pop off" of the injection site when, for example, a needle is being withdrawn from the site after penetrating it.

DESCRIPTION OF THE INVENTION

In accordance with this invention, a unitary molded injection site is provided, formed of self-sealing, pierca-ble, resilient material, in which the injection site comprises a central, needle-receiving portion, and a skirt portion contiguous therewith and extending, in its original, unstressed configuration in a first direction therefrom.

The injection site may be placed on the end of a support tube by temporarily convoluting the skirt portion in a direction, opposed to the first direction, out of its original, unstressed configuration into a position about the central portion, to expose an inner surface of the central portion. The end of the support tube may then be brought adjacent to the inner surface. Following this, the skirt portion is brought back out of convoluted configuration towards its original, unstressed configuration, with the skirt portion surrounding the end portion of the tube in telescoping relation. As a result of this, the injection site is positioned on the support tube in relatively unstressed condition, which improves its resistance to being accidentally removed by the pulling forces of an injection needle which has penetrated the injection site and is being withdrawn, or other accidental forces that might tend toward removal of the injection site from the support tube.

Preferably, a prior step may be performed of heat sealing a needle-piercable membrane across the outer end of the support tube, while simultaneously flaring the outer end of the tube, prior to surrounding the end with the skirt portion. The flared end of the support tube can interact with a plurality of sealing rings which may be defined on the inner surface of the skirt portion in its original, unstressed configuration, in which the rings are adapted to sealingly bear against the support tube. If withdrawing forces on the injection site tend to cause it to start to be removed, the uppermost sealing ring will engage the flared outer end of the support tube, preventing accidental removal of the injection site from the tube. The flared end may extend in annular relation outwardly from the tube in generally perpendicular relation thereto, with the sealing rings being positioned all on one side of the flared end.

It is also desirable for the central, needle-receiving portion to be at least one half as thick as it is wide, to provide resealing characteristics after penetration by an injection needle.

Referring to the drawings.

Figure 3:
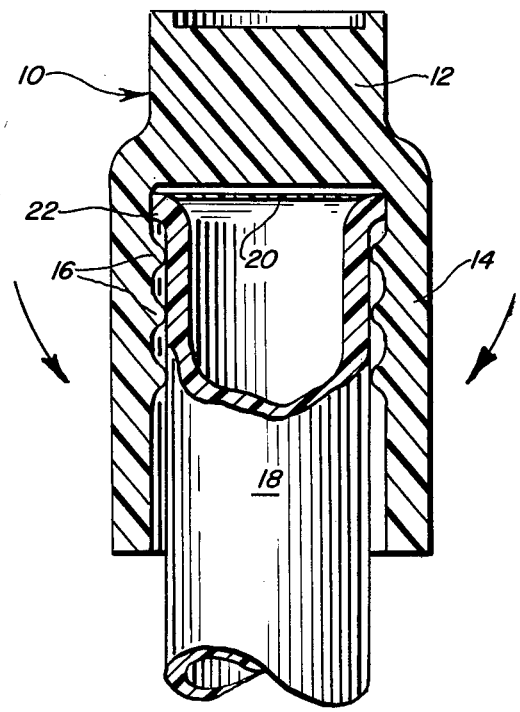

FIG. 3 is an elevational view, taken partly in vertical section and with portions broken away, showing the further step of the installation method of this invention in which the skirt portion is brought back toward its original, unstressed configuration while surrounding the end portion of the tube in telescoping relation, so that the injection site is positioned on the support tube in relatively unstressed condition.

Referring to the drawings, unitary molded injection site 10, which may be made of natural latex, is shown to comprise a central, needle-receiving portion 12 which preferably is at least one half as thick as it is wide to provide abundant resealing capability against needle penetration. Tubular skirt portion 14 is contiguous with central portion 12, and extends in a first direction from the central portion 12. A plurality of sealing rings 16 may be provided as desired, and are adapted to sealingly bear against support tube 18 after installation of the injection site 10 on tube 18.

Support tube 18 may carry a sealed, needle-piercable membrane 20 across the bore of the tube adjacent its flared end 22. Needle-piercable membrane 20 may be made, for example, of polyvinylchloride and may have a thickness of about 0.003 to 0.01 inch, preferably about 0.005 inch.

The support tube 18 and membrane 20 may be assembled by a heat-sealing step which may simultaneously produce the flare 22 of the outer end of tube 18, prior to applying injection site 10.

Figure 1:
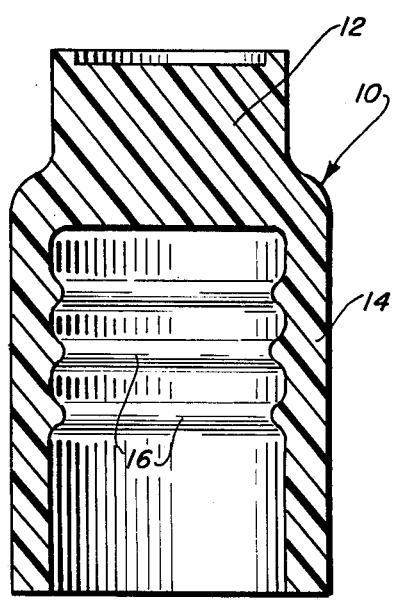
FIG. 1 is a vertical sectional view of the unitary, molded injection site of this invention in its original, as-molded, unstressed configuration.
Figure 2:
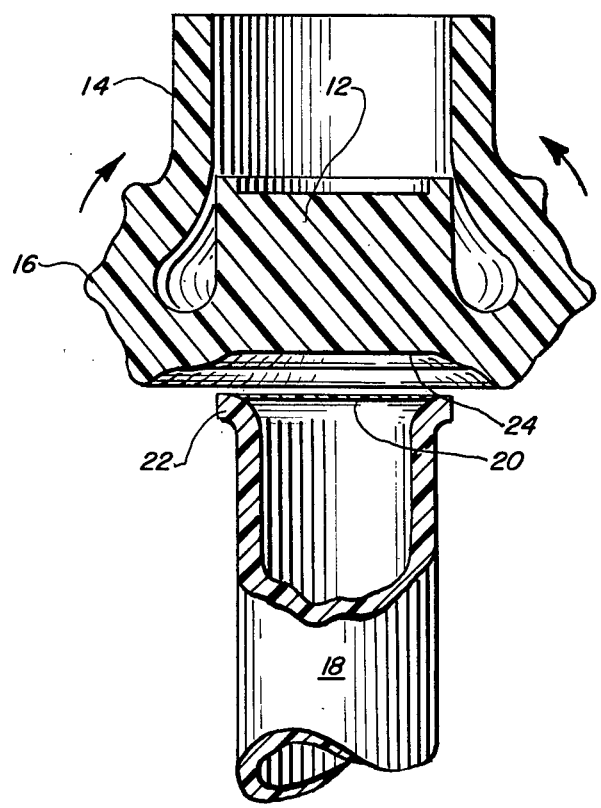
FIG. 2 is an elevational view, taken partly in vertical section and with portions broken away, showing how the skirt of the injection site can be convoluted about the central portion and how the end of the support tube may be brought adjacent the inner surface of the central portion.

FIG. 2 shows initial steps of the injection site application process. Skirt portion 14 is convoluted in a direction opposed to the first direction out of its original, unstressed configuration into a position surrounding central portion 12. The flared end 22 of support tube 18 may then be brought adjacent the inner surface 24 of the central portion 12.

Thereafter, as shown in FIG. 3, the skirt portion 14 may be unconvoluted again, to bring it back toward its original, unstressed configuration, with the skirt portion surrounding convoluted end 22 of tube 18 in telescoping relation. This brings sealing rings 16 into sealing relation against the exterior of support tube 18. As a result of this, the injection site 10, as shown in FIG. 3, is positioned on support tube 18 in relatively unstressed condition when compared with, for example, the injection site of U.S. Pat. No. 4,133,441. The result of this is to cause injection site 10 to be much less capable of accidental removal from the end of tube 18, since the forces present, if any, urging skirt 14 to roll upwardly out of telescoping relation with tube 18, are greatly reduced and possibly non-existent. In fact, the residual stresses of the mounted injection site will primarily be directed toward squeezing tube 18, and resisting roll up and pop off, since injection site 10 will be in essentially unstressed, as-molded configuration.

When a needle pierces injection site 10 it passes through central portion 12 and membrane 20 for access to tube 18. Tube 18 may be part of any desired type of medical device, as specified above, for example, a parenteral solution bag, a parenteral solution set, etc.

Membrane 20 is provided to assure the cleanliness of the interior of tube 18 prior to application of injection site 10, and also to provide a further guarantee of sterility after application of the injection site but before needle penetration has taken place.

The needle may then be withdrawn, with sealing taking place in the thick mass of central portion 12 in reliable, aseptic manner.

The above has been offered for illustrative purposes only and is not intended to limit the scope of the invention, which is as defined in the claims below.

That which is claimed is:

1. A molded injection site, formed of self-sealing, needle-pierceable, resilient material, comprising a central needle-receiving portion and a tubular skirt portion contiguous therewith and extending in a first direction therefrom in its original, unstressed condition, said skirt portion surrounding and gripping the end of a support tube in telescoping relation thereto while extending in first direction, said skirt portion defining, on its inner surface, a plurality of sealing rings adapted to sealingly bear against said support tube, said support tube defining a flared end extending in annular relation outwardly from said tube in generally perpendicular relation thereto, said sealing rings being positioned all on one side of said flared end, said flared end being surrounded by said skirt, whereby, on the attempted removal of the injection site, the uppermost sealing ring will engage the flared end of said support tube, preventing accidental removal of the injection site from the support tube.

2. The injection site of claim 1 in which said central, needle-receiving portion is at least one half as thick as it is wide.

3. The injection site of claim 2 in which said self-sealing, needle-piercable, resilient material is natural rubber latex.

4. The injection site of claim 1 in which the outer end of said support tube carries a sealed, needle-piercable membrane across the end of said tube adjacent said flared end.

5. The injection site of claim 1 in which the outer end of said support tube carries a sealed, needle-pierceable membrane across the bore of said tube in close proximity to said injection site.

* * * * *